(12) United States Patent
Chen et al.

(10) Patent No.: US 10,690,659 B2
(45) Date of Patent: Jun. 23, 2020

(54) MEASURING PHYSICAL AND BIOCHEMICAL PARAMETERS WITH MOBILE DEVICES

(71) Applicant: IXENSOR CO., LTD., Taipei (TW)

(72) Inventors: Yenyu Chen, Taipei (TW); Tungmeng Tsai, Taipei (TW); Chieh Hsiao Chen, Taipei (TW); Hungchih Wang, Taipei (TW); Yuwei Tang, Taipei (TW); Chiachun Hung, Taipei (TW); Chihchieh Wu, Taipei (TW)

(73) Assignee: IXENSOR CO., LTD., Taipei (TW)

( * ) Notice: Subject to any disclaimer, the term of this patent is extended or adjusted under 35 U.S.C. 154(b) by 0 days.

(21) Appl. No.: 15/489,747

(22) Filed: Apr. 18, 2017

(65) Prior Publication Data

US 2017/0219569 A1    Aug. 3, 2017

Related U.S. Application Data

(63) Continuation of application No. 14/528,100, filed on Oct. 30, 2014, now Pat. No. 9,658,217.
(Continued)

(51) Int. Cl.
*G01N 33/52*      (2006.01)
*H04M 1/18*       (2006.01)
(Continued)

(52) U.S. Cl.
CPC ....... *G01N 33/525* (2013.01); *G01N 33/4875* (2013.01); *H04B 1/3888* (2013.01);
(Continued)

(58) Field of Classification Search
CPC .. G01N 33/525; G01N 21/78; G01N 21/8483; G01N 33/4875; A61B 5/6898;
(Continued)

(56) References Cited

U.S. PATENT DOCUMENTS 6,602,469 B1   8/2003   Maus et al.
7,767,149 B2   8/2010   Maus et al.
(Continued)

FOREIGN PATENT DOCUMENTS

CA   2601720 A1   10/2006
CA   2601720 C    8/2014
(Continued)

OTHER PUBLICATIONS

International Search Report and Written Opinion of the International Searching Authority, International application No. PCT/CN2015/073163, dated May 25, 2015.
(Continued)

*Primary Examiner* — Samuel P Siefke
(74) *Attorney, Agent, or Firm* — SU IP Consulting

(57) ABSTRACT

A method for a mobile computing device with a camera and a screen to measure a test strip in a test strip module includes, in a calibration phase before a sample is introduced to a reaction area on the test strip, detecting with the camera an ambient light effect when the test strip module is mounted on the face of the mobile computing device. In a measurement phase after the sample is introduced to the reaction area on the test strip, the method also includes illuminating the test strip with a light provided by a light source area on the screen, detecting with the camera one or more colors of the reaction area, correcting the detected one or more colors for the ambient light effect, correlating the corrected one or more colors to an analyte property, and displaying a value of the analyte property on the screen.

14 Claims, 13 Drawing Sheets

Related U.S. Application Data

(60) Provisional application No. 61/940,500, filed on Feb. 17, 2014, provisional application No. 61/944,306, filed on Feb. 25, 2014, provisional application No. 62/025,883, filed on Jul. 17, 2014, provisional application No. 62/044,886, filed on Sep. 2, 2014.

(51) Int. Cl.
| | | |
|---|---|---|
| *G01N 33/487* | (2006.01) | |
| *H04B 1/3888* | (2015.01) | |
| *H04M 1/02* | (2006.01) | |
| *H04M 1/21* | (2006.01) | |
| *G06T 7/90* | (2017.01) | |
| *H04N 17/02* | (2006.01) | |

(52) U.S. Cl.
CPC ............... *H04M 1/185* (2013.01); *G06T 7/90* (2017.01); *H04M 1/0254* (2013.01); *H04M 1/0264* (2013.01); *H04M 1/21* (2013.01); *H04M 2250/52* (2013.01); *H04N 17/02* (2013.01)

(58) Field of Classification Search
CPC ...... H04M 1/0254; H04M 1/21; H04M 1/185; H04M 2250/52; H04B 1/3888; G06T 7/90; H04N 17/02
See application file for complete search history.

(56) References Cited

U.S. PATENT DOCUMENTS

| | | |
|---|---|---|
| 8,145,431 B2 | 3/2012 | Kloepfer et al. |
| 8,257,654 B2 | 9/2012 | Maus et al. |
| 8,935,007 B2 | 1/2015 | Kloepfer et al. |
| 2006/0222567 A1 | 10/2006 | Kloepfer et al. |
| 2007/0183930 A1 | 8/2007 | Roman |
| 2012/0112031 A1 | 5/2012 | Gormick et al. |
| 2012/0183442 A1 | 7/2012 | Kloepfer et al. |
| 2012/0309469 A1 | 12/2012 | Fornara |
| 2013/0041691 A1 | 2/2013 | Maus et al. |
| 2013/0116831 A1 | 5/2013 | Rogers et al. |
| 2013/0203043 A1 | 8/2013 | Ozcan et al. |
| 2013/0273528 A1 | 10/2013 | Ehrenkranz |
| 2014/0013387 A1 | 1/2014 | Vangpat et al. |
| 2014/0072189 A1* | 3/2014 | Jena ................... G01N 21/8483 382/128 |
| 2014/0120563 A1 | 5/2014 | Ozcan et al. |
| 2014/0193839 A1* | 7/2014 | Cunningham ............ G01J 3/28 435/7.92 |
| 2015/0233898 A1 | 8/2015 | Chen et al. |

FOREIGN PATENT DOCUMENTS

| | | |
|---|---|---|
| CN | 1667418 A | 9/2005 |
| CN | 102348986 A | 2/2012 |
| CN | 102377851 A | 3/2012 |
| EP | 1710565 A1 | 10/2006 |
| EP | 1866637 A2 | 12/2007 |
| EP | 1866637 A4 | 7/2013 |
| GB | 2483482 A | 3/2012 |
| JP | 2010190867 A | 9/2010 |
| TW | 201018907 A | 5/2010 |
| TW | M492136 U | 12/2014 |
| WO | 0137195 A2 | 5/2001 |
| WO | 0137195 A3 | 5/2001 |
| WO | 2006107666 A2 | 10/2006 |
| WO | 2006107666 A3 | 6/2007 |
| WO | 2013119266 A1 | 8/2013 |
| WO | 2013149598 A1 | 10/2013 |

OTHER PUBLICATIONS

Onur Mudanyali et al., "Integrated Rapid-Diagnostic-Test Reader Platform on a Cellphone", Lab Chip, 2012, pp. 2678-2686, vol. 12.
The Partial Suuplementary European Search Report, Application No. 15749286.9, dated Sep. 22, 2017.
The Extended European Search Report, Application No. 15749286.9, dated Jan. 25, 2018.
The Extended European Search Report, Application No. 19160024.6, dated Jun. 18, 2019.

* cited by examiner

MEASURING PHYSICAL AND BIOCHEMICAL PARAMETERS WITH MOBILE DEVICES

CROSS-REFERENCE TO RELATED APPLICATIONS

This application is a continuation under 35 U.S.C. § 120 of U.S. patent application Ser. No. 14/528,100, filed Oct. 30, 2014, which claims the benefit of U.S. Provisional Application No. 61/940,500, filed Feb. 17, 2014, U.S. Provisional Application No. 61/944,306, filed Feb. 25, 2014, U.S. Provisional Application No. 62/025,883 filed Jul. 17, 2014, and U.S. Provisional Application No. 62/044,886 filed Sep. 2, 2014. The U.S. Patent Application and the U.S. Provisional Applications, including any appendices or attachments thereof, are incorporated by reference herein in their entirety.

FIELD

The present disclosure generally relates to methods and systems for photometric analysis an analyte on a test strip

BACKGROUND

A specimen test strip has a reaction area containing reagents that react with an analyte in a specimen sample, such as cholesterol or glucose in a blood sample. The reaction area changes color according to a property of the analyte, such as the cholesterol or glucose level in blood. The specimen test strip is inserted into a meter that optically determines the characteristic of the analyte.

SUMMARY

In examples of the present disclosure, a method for a mobile computing device with a camera and a screen to measure a test strip in a test strip module is disclosed. The method includes, in a calibration phase before a sample is introduced to a reaction area on the test strip, detecting with the camera an ambient light effect when the test strip module is mounted on the face of the mobile computing device. In a measurement phase after the sample is introduced to the reaction area on the test strip, the method also includes illuminating the test strip with a light provided by a light source area on the screen, detecting with the camera one or more colors of the reaction area, correcting the detected one or more colors for the ambient light effect, correlating the corrected one or more colors to an analyte property, and displaying a value of the analyte property on the screen.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are therefore not to be considered limiting of its scope. The disclosure will be described with additional specificity and detail through use of the accompanying drawings.

In the drawings.

DETAILED DESCRIPTION

As used herein, the term "includes" means includes but not limited to, the term "including" means including but not limited to. The terms "a" and "an" are intended to denote at least one of a particular element. The term "based on" means based at least in part on. The term "or" is used to refer to a nonexclusive such that "A or B" includes "A but not B," "B but not A," and "A and B" unless otherwise indicated.

Figure 1:
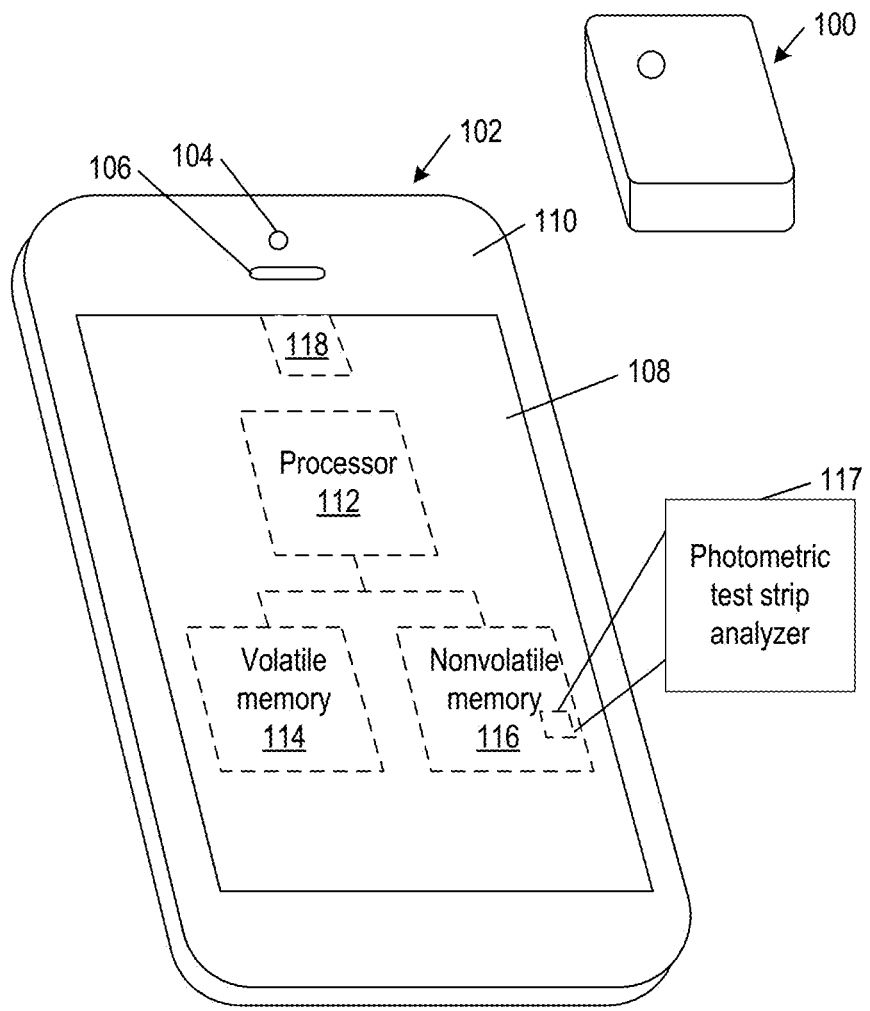
FIG. 1 illustrates a top isometric view of a test strip module to be used with a mobile computing device in examples of the present disclosure.

FIG. 1 illustrates a top isometric view of a test strip module 100 to be used with a mobile computing device 102 in examples of the present disclosure. Mobile computing device 102 has a camera 104, an ear speaker 106, and a screen 108 on a face 110 (e.g., a front face) of mobile computing device 102. On face 110, camera 104 may be located above ear speaker 106. Ear speaker 106 may have the form of a hole (as shown) or a protrusion above face 110 (not shown). Mobile computing device 102 includes a processor 112, a nonvolatile memory 114, and a volatile memory 116. Nonvolatile memory 114 stores the code for a photometric test strip analyzer 117. Mobile computing device 102 may be a mobile phone, a tablet computer, or a laptop computer. Hereafter a "mobile phone 102" is used to represent variations of mobile computing device 102.

Figure 2:
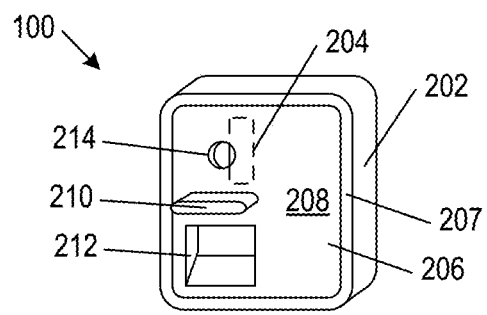
FIG. 2 illustrates a bottom isometric view of the test strip module of FIG. 1 in examples of the present disclosure.

FIG. 2 illustrates a bottom isometric view of test strip module 100 in examples of the present disclosure. Test strip module 100 has a case 202 with an open bottom, a test strip 204 (shown in phantom) held inside case 202, and a bottom cover 206 that closes the open bottom of case 202. Case 202 has a bottom surface 207 and bottom cover 206 has a bottom surface 208 that may or may not be even with bottom surface 207 of case 202. Bottom cover 206 also has a position feature 210, which may be a position anchor that extends down past a mating surface of test strip module 100 to face 110 of mobile phone 102. The mating surface may be bottom surface 207 or 208. Position anchor 210 has a shape matching a corresponding feature on face 110 (FIG. 1) of mobile phone 102 (FIG. 1), such as ear speaker hole 160 (FIG. 1). Position anchor 210 may have a rectangular or an obround shape.

Bottom cover 206 defines a light port 212 and a camera port 214. Light port 212 allows light emitted by a light source area 118 (FIG. 1) of screen 108 to enter test strip module 100 and illuminate the interior of test strip module 100, including a reaction area on test strip 204. Camera port 214 allows camera 104 (FIG. 1) of mobile phone 102 to capture images inside test strip module 100, including the reaction area on test strip 204. Camera port 214 may be located above position anchor 210 to match the configuration of camera 104 and a feature corresponding to position anchor 210 on mobile phone 102, such as ear speaker hole 106. Light port 212 and camera port 214 may be holes or windows.

Figure 3:
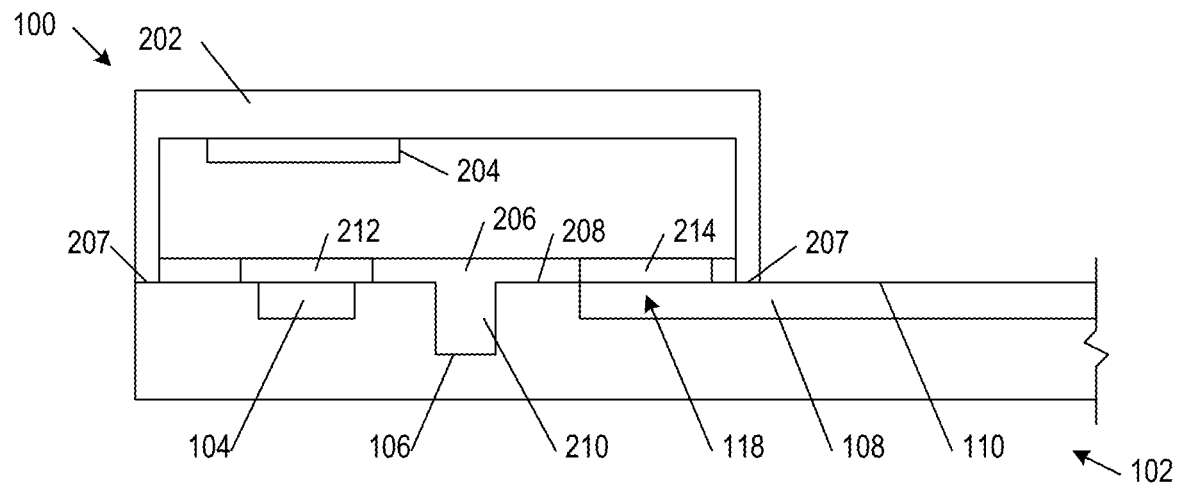
FIG. 3 illustrates a cross-sectional view of the test strip module of FIG. 1 on the mobile computing device of FIG. 1 in examples of the present disclosure.

FIG. 3 illustrates a cross-sectional view of test strip module 100 on mobile phone 102 in examples of the present disclosure. In use, a user rests mobile phone 102 flat on a horizontal surface and places test strip module 100 on face 110 of mobile phone 102. The user then slides test strip module 100 around on face 110 until position anchor 210 engages the corresponding feature on face 110, such as fitting into ear speaker hole 106. When position anchor 210 fits into ear speaker hole 106, mating surface 207 or 208 may come into intimate contact with face 110, and camera port 214 and light port 212 become properly aligned with camera 104 and light source area 118, respectively. Note the exact shape and location of position anchor 210 depends on the configuration of camera 104 and ear speaker 106 of mobile phone 102.

Figure 4:
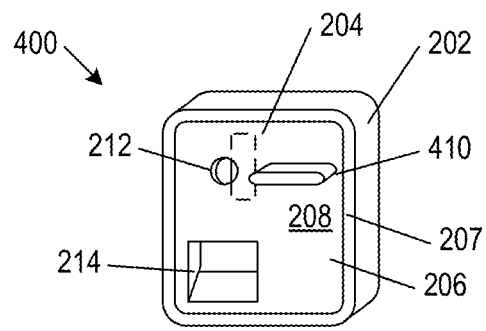
FIG. 4 illustrates a variation of the test strip module of FIG. 1 in examples of the present disclosure.

FIG. 4 illustrates a variation 400 of test strip module 100 (FIG. 1) in examples of the present disclosure. Test strip module 400 is similar to test strip module 100 except position anchor 210 has been replaced by a position anchor 410 at a different location to match the location of a corresponding feature, such as the ear speaker hole, on the face of another mobile phone.

Figure 5:
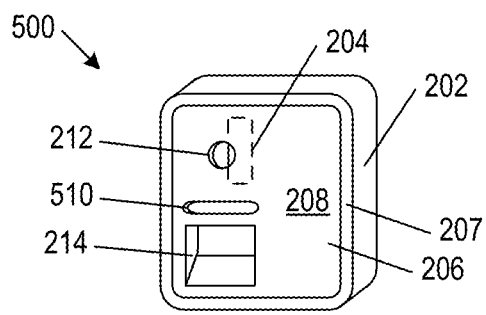
FIG. 5 illustrates a variation of the test strip module of FIG. 1 in examples of the present disclosure.

FIG. 5 illustrates a variation 500 of test strip module 100 (FIG. 1) in examples of the present disclosure. Test strip module 500 is similar to test strip module 100 except position anchor 210 has been replaced by a position feature 510, which may be a position hole defined by bottom cover 206. Position hole 510 matches the configuration of a corresponding feature, such as a protruding ear speaker, on the face of another mobile phone. In use, a user slides test strip module 500 around on the face of the mobile phone until position hole 510 engages the corresponding feature on the face of the mobile phone, such as receiving the ear speaker protrusion. When position hole 510 receives the ear speaker protrusion, mating surface 207 or 208 may come into intimate contact with the face of the mobile phone, and camera port 214 and light port 212 become properly aligned with the camera and the light source area on the face of the mobile phone, respectively.

Figure 6:
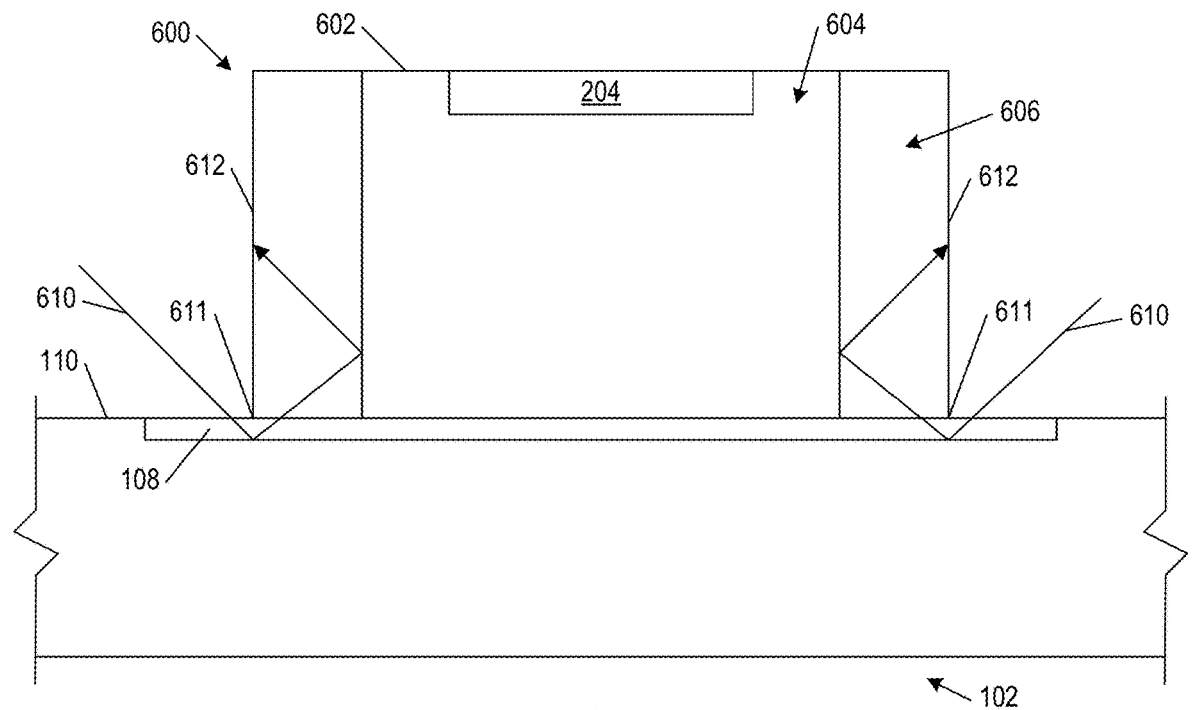
FIG. 6 is a cross-sectional view of a test strip module with inner and outer compartments in examples of the present disclosure.

FIG. 6 is a cross-sectional view of a test strip module 600 in examples of the present disclosure. Test strip module 600 may be a variation of another test strip module in the present disclosure so test strip module 600 may share elements with the other test strip module. Test strip module 600 has a case 602 with an open bottom, an inner compartment 604, and an outer compartment 606 that surrounds at least part of inner compartment 604. Test strip 204 is located in inner compartment 604 and outer compartment 606 shields test strip 204 from ambient light 610 that may leak in through an interface 611 between a perimeter wall 612 of case 602 and face 110 of mobile phone 102 onto which test strip module 600 is placed. Outer compartment 606 traps and absorbs ambient light 610 so ambient light 610 does not illuminate test strip 204 in inner compartment 604. Outer compartment 606 may have a texture or be formed of a material that absorbs light. Without outer compartment 606, ambient light 610 may interfere with the expected illumination from light source area 118 (FIG. 3) of screen 108 on face 110.

Figure 7:
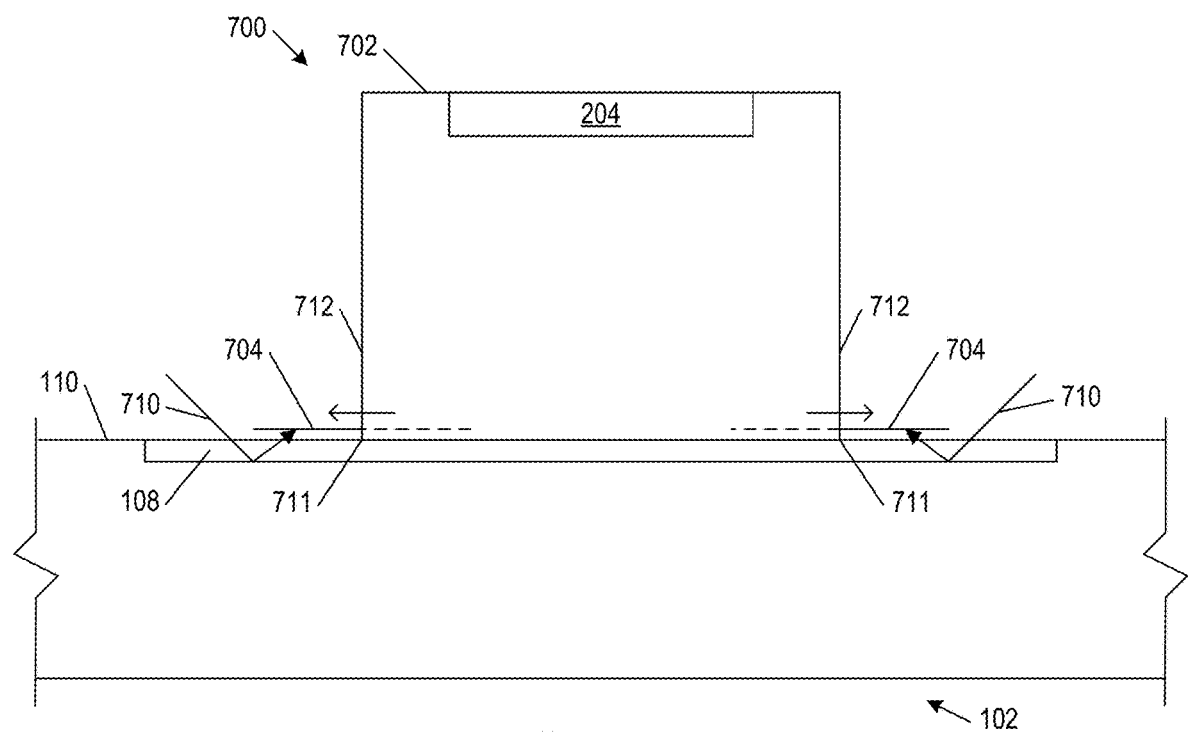
FIG. 7 is a cross-sectional view of a test strip module with a skirt in examples of the present disclosure.

FIG. 7 is a cross-sectional view of a test strip module 700 in examples of the present disclosure. Test strip module 700 may be a variation of another test strip module in the present disclosure so test strip module 700 may share elements with the other test strip module. Test strip module 700 has a case 702 with a perimeter wall 712 and a skirt 704 around at least part of perimeter wall 712. Test strip 204 is located in case 702 and skirt 704 shields test strip 204 from ambient light 710 that may leak in through an interface 711 between perimeter wall 712 and face 110 of mobile phone 102 onto which test strip module 700 is placed. Skirt 704 may lie flat against face 110 of mobile phone 102. Skirt 704 traps and absorbs ambient light 710 so ambient light 710 does not illuminate test strip 708. Skirt 704 may have a texture or be formed of a material that absorbs light. Without skirt 704, ambient light 710 may interfere with the expected illumination from light source area 118 (FIG. 3) of screen 108 on face 110.

In some examples of the present disclosure, skirt 704 is a slide engaged to case 702. Skirt 704 may be initially stored in a retracted position inside case 702 (shown in phantom). In use, skirt 704 may slide out from the retracted position to an extended position outside of case 702.

Figure 8:
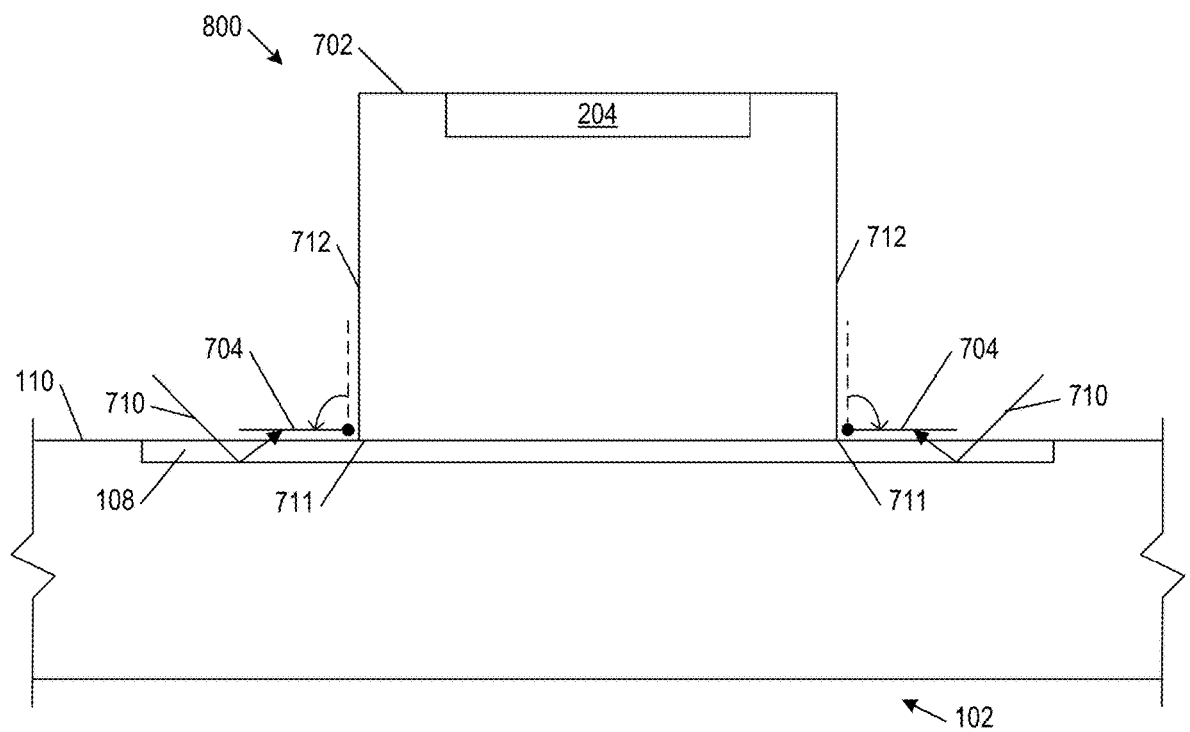
FIG. 8 is a cross-sectional view of a test strip module with a skirt in examples of the present disclosure.

FIG. 8 is a cross-sectional view of a test strip module 800 in examples of the present disclosure. Test strip module 800 is similar to test strip module 700 except skirt 704 is now hinged to perimeter wall 712 of case 702. Skirt 704 may be initially stored in an upright position against perimeter wall 712 of case 702 (shown in phantom). In use, skirt 704 may rotate from the upright position to a horizontal position against face 110 of mobile phone 102 onto which test strip module 800 is placed.

Figure 9:
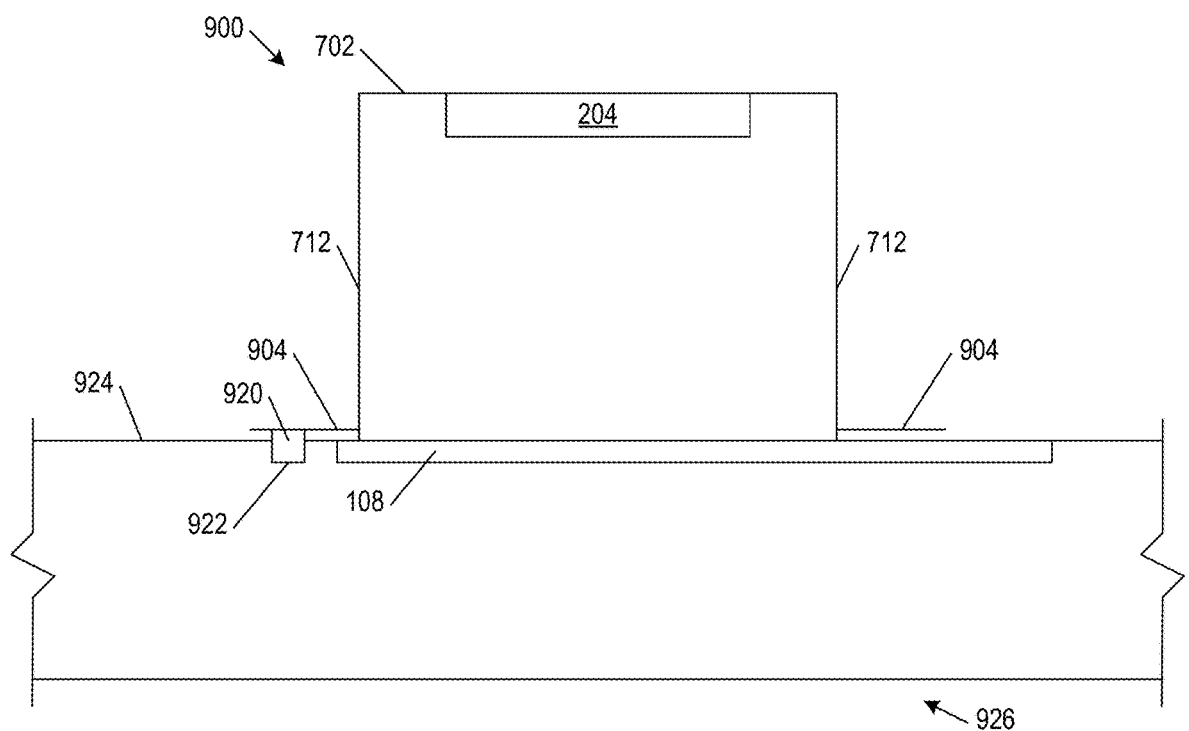
FIG. 9 is a cross-sectional view of a test strip module with a position anchor on a skirt in examples of the present disclosure.

FIG. 9 is a cross-sectional view of a test strip module 900 in examples of the present disclosure. Test strip module 900 may be a variation of another test strip module in the present disclosure so test strip module 900 may share elements with the other test strip module. Test strip module 900 has a skirt 904 around at least part of perimeter wall 712 of case 702. Skirt 904 may be similar to skirt 704 (FIG. 7 or 8). Instead of a bottom cover with a position anchor or position hole, skirt 904 has a position anchor 920 that extends downward from skirt 904 and fits into a matching hole 922 on a face 924 of a portable computing device 926. Alternatively skirt 904 defines a position hole (not shown) that receives a matching protrusion (not shown) on face 924.

Figure 10:
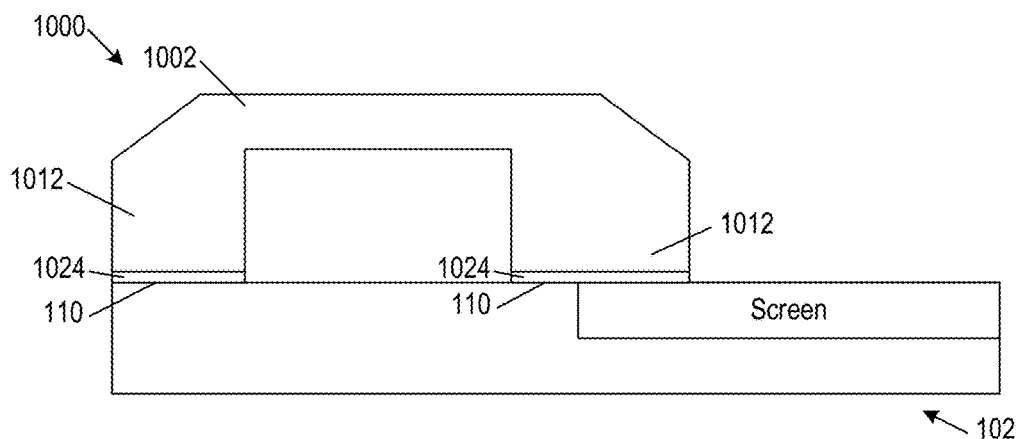
FIG. 10 is a cross-sectional view of a test strip module with a fine or pliant bottom interface to a face of a mobile computing device in examples of the present disclosure.

FIG. 10 is a cross-sectional view of a test strip module 1000 in examples of the present disclosure. Test strip module 1000 may be a variation of another test strip module in the present disclosure so test strip module 600 may share elements with the other test strip module. Test strip module 1000 includes a case 1002 with a perimeter wall 1012. Perimeter wall 1012 has a bottom interface 1024 that comes into intimate contact with face 110 of portable computing device 102 to prevent ambient light from entering through any gap between bottom interface 1024 and face 110. In some examples, bottom interface 1024 is sanded or otherwise processed smooth to have a roughness of 100 microns. In other examples, bottom interface 1024 may be a pliant material, such as a polyurethane soft-touch coating, fixed to the body of perimeter wall 1012.

Figure 11:
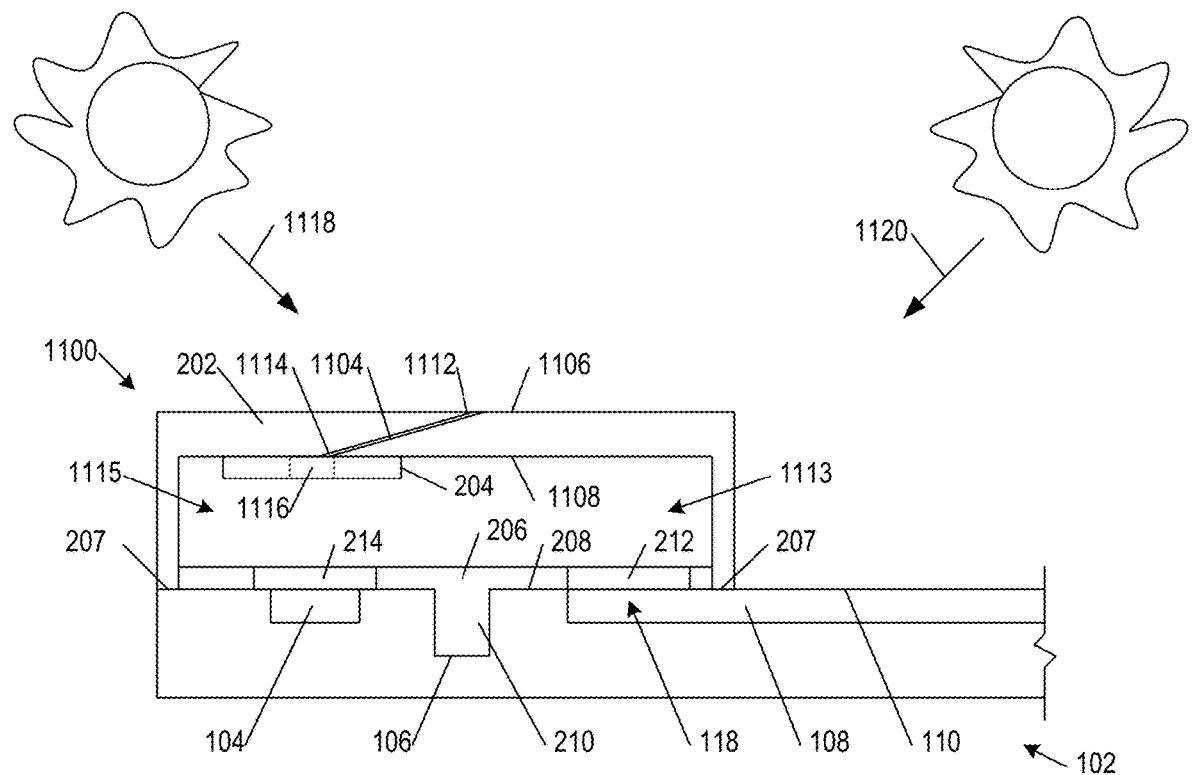
FIG. 11 is a cross-sectional view of a test strip module with a slanted sample channel in examples of the present disclosure.

FIG. 11 is a cross-sectional view of a test strip module 1100 in examples of the present disclosure. Test strip module 1100 may be a variation of another test strip module in the present disclosure so test strip module 1100 may share elements with the other test strip module. Test strip module 1100 includes case 202 with the open bottom, test strip 204 held inside case 202, and bottom cover 206 that closes the open bottom of case 202. Case 202 defines a sample (e.g., blood) channel 1104 from the exterior to the interior of case 202, such as from a roof 1106 to a ceiling 1108. Sample channel 1104 is sloped relative to mating surface 207 or 208. Sample channel 1104 has an upper end 1112 with an inlet and a lower end 1114 with an outlet. A sample enters the inlet at upper end 1112, travels through sample channel 1104, exits through the outlet at lower end 1114, and enters a reaction area 1116 on test strip 204.

Sample channel 1104 is oriented so lower end 1114 is located in or proximate to a first end 1115 of test strip module 1100 with test strip 204 and camera port 214, and upper end 1112 is located in or proximate to a second end 1113 of test strip module 1100 with camera port 214. First end 1115 may be a distal end away from a user while second end 1113 may be a proximate end close to the user. When ambient light 1118 is coming from the front (or the side) of a user during use, an ambient light 1118 would be misaligned with sample channel 1104 and therefore unable to enter test strip module 1100 through sample channel 1104. When an ambient light 1120 is coming from the back of the user, ambient light 1120 would be blocked by the user and therefore unable to enter test strip module 1100 through sample channel 1104.

Figure 12:
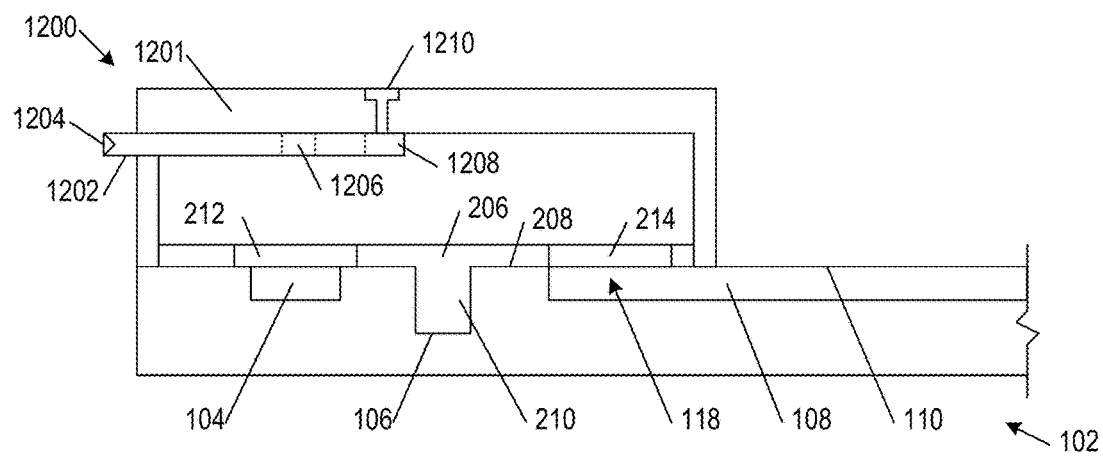
FIG. 12 is a cross-sectional view of a test strip module with a sample observation window in examples of the present disclosure.

FIG. 12 is a cross-sectional view of a test strip module 1200 in examples of the present disclosure. Test strip module 1200 may be a variation of another test strip module in the present disclosure so test strip module 1200 may share elements with the other test strip module. Test strip module 1200 includes a case 1201 with an open bottom, a test strip 1202 located both inside and outside of case 1201, and bottom cover 206 that closes the open bottom of case 1201. Test strip 1202 has a tip 1204 located outside of case 1201 to receive a sample, and a reaction area 1206 and a reservoir 1208 located inside case 1201. The sample travels to reaction area 1206, and a part of the sample travels further downstream to reservoir 1208. Case 1201 includes an observation window 1210 to reservoir 1208. When a user sees the sample in observation window 1210, the user knows test strip 1202 has receives a sufficient sample amount.

Figure 13:
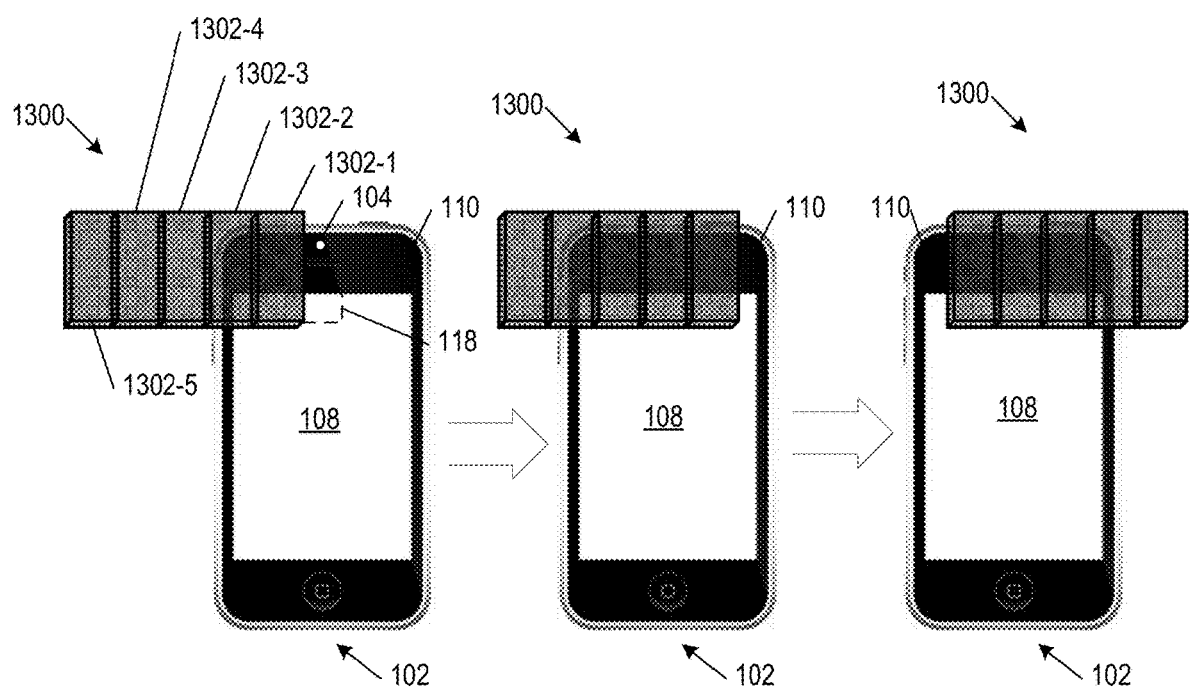
FIG. 13 is a top view of a test strip package in examples of the present disclosure.

FIG. 13 is a top view of a test strip package 1300 in examples of the present disclosure. Test strip package 1300 includes multiple test strip modules, such as test strip modules 1302-1, 1302-2, 1302-3, 1302-4, and 1302-5 (collectively as "test strip modules 1302" or individually as a generic test strip module "1302"). Each test strip module 1302 may be similar to any test strip module described in the present disclosure. Test strip modules 1302 may share a common case and a common bottom cover. The case may have multiple compartments that each holds a test strip. The case is slidably engaged with the bottom cover. The bottom cover defines a camera port and a light port. The bottom cover has a position feature, such as a position anchor or hole, that engages a matching feature, such as an ear speaker hole or protrusion, on face 110 of mobile phone 102 to align the camera port and the light port on the bottom cover to camera 104 (FIG. 1) and light source area 118 (FIG. 1) on screen 108 (FIG. 1) of mobile phone 102.

The case may slide over the bottom cover to place one compartment at a time over the camera port and the light port as shown in FIG. 13. The position of the compartment over the camera port and the light port may be defined by latching mechanism, such as snap fit protrusions and depressions, on the case and the bottom cover. When one compartment is in position, the adjacent compartment or compartments may shield that compartment from ambient light.

Figure 14:
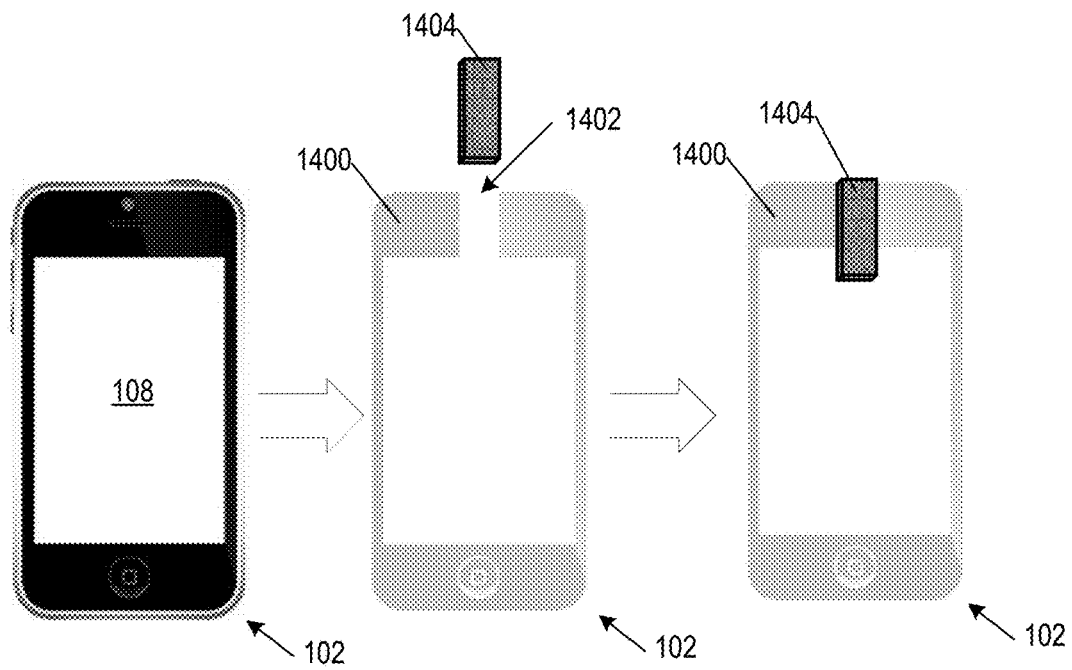
FIG. 14 is a top view of a screen protector with a slot to receive a test strip module in examples of the present disclosure.

FIG. 14 is a top view of a screen protector 1400 for mobile phone 102 in examples of the present disclosure. Screen protector 1400 defines a slot or cutout 1402 to receive and position a test strip module 1404 over camera 104 (FIG. 1) and light source area 118 (FIG. 1) on screen 108 of mobile phone 102. Test strip module 1404 may be any test strip module described in the present disclosure.

Figure 15:
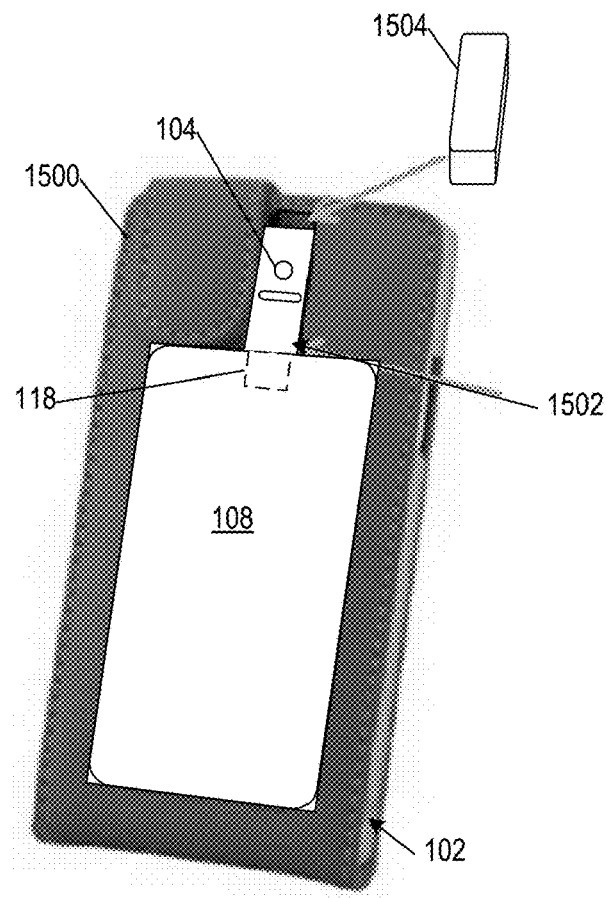
FIG. 15 is a top isometric view of a protective case with a slot to receive a test strip module in examples of the present disclosure.

FIG. 15 is a top isometric view of a protective case 1500 for mobile phone 102 in examples of the present disclosure. Protective case 1500 defines a slot or cutout 1502 to receive and position a test strip module 1504 over camera 104 (FIG. 1) and light source area 118 (FIG. 1) on screen 108 of mobile phone 102. Test strip module 1504 may be any of the test strip modules described in the present disclosure.

Figure 16:
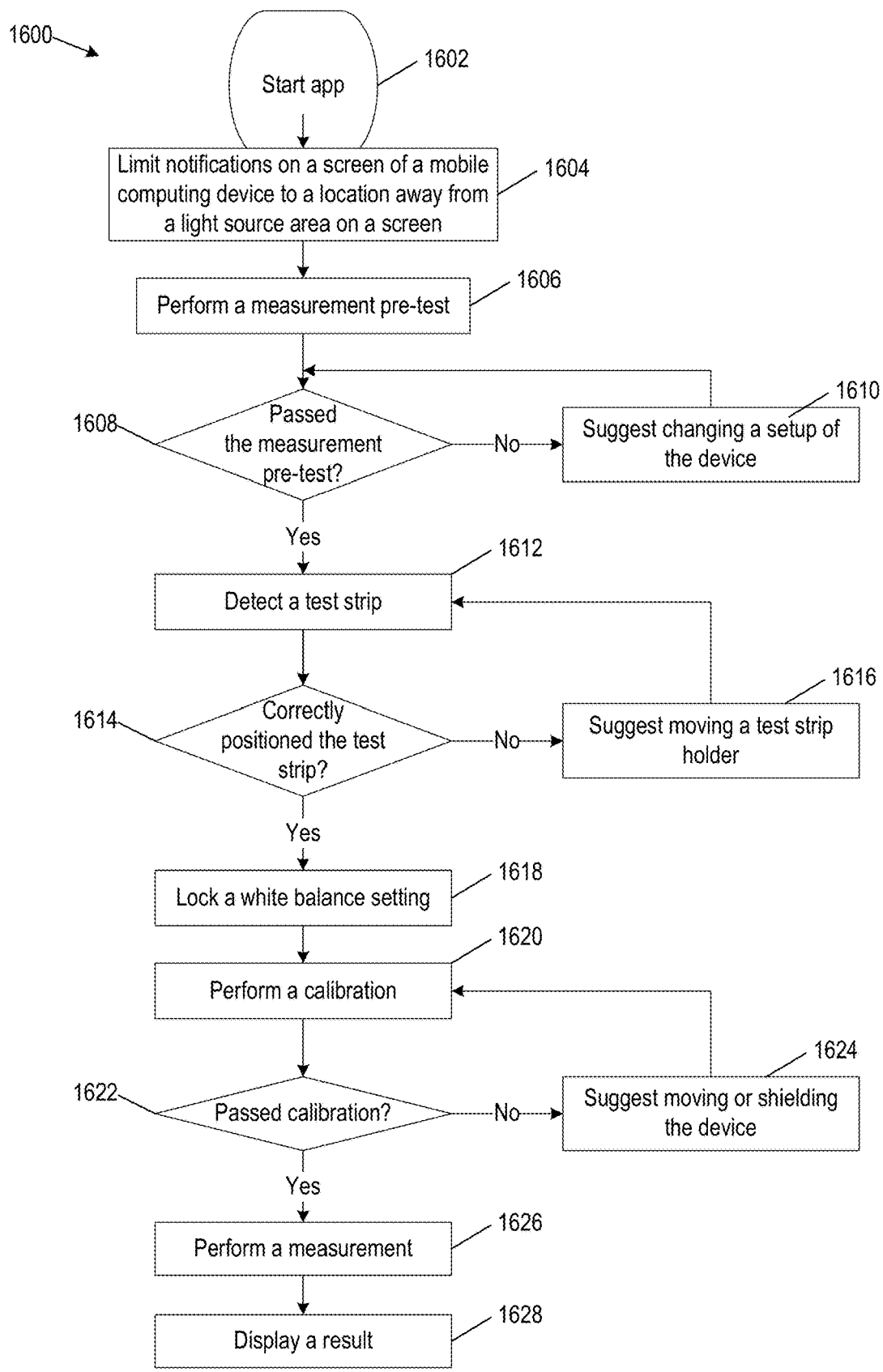
FIG. 16 is a flowchart of a method for a photometric test strip analyzer executed by a processor in the mobile computing device of FIG. 1 to determine an analyte property from a test strip in a test strip module in examples of the present application.

FIG. 16 is a flowchart of a method 1600 for photometric test strip analyzer 117 (FIG. 1) executed by processor 112 (FIG. 1) on mobile phone 102 to determine an analyte property (e.g., cholesterol or glucose level) from a test strip in a test strip module (e.g., test strip 204 in test strip module 100 in FIG. 1) in examples of the present application. Method 1600 may include one or more operations, functions, or actions illustrated by one or more blocks. Although the blocks of method 1600 and other methods described herein are illustrated in sequential orders, these blocks may also be performed in parallel, or in a different order than those described herein. Also, the various blocks may be combined into fewer blocks, divided into additional blocks, or eliminated based upon the desired implementation. Method 1600 may begin in block 1602.

In block 1602, processor 112 receives user input to run photometric test strip analyzer 117. In response processor 112 executes the code for photometric test strip analyzer 117. Block 1602 may be followed by block 1604.

In block 1604, processor 112 limits notifications (e.g., banners) on mobile phone 102 to a location away from light source area 118 (FIG. 1) on screen 108 (FIG. 1).

Figure 17:
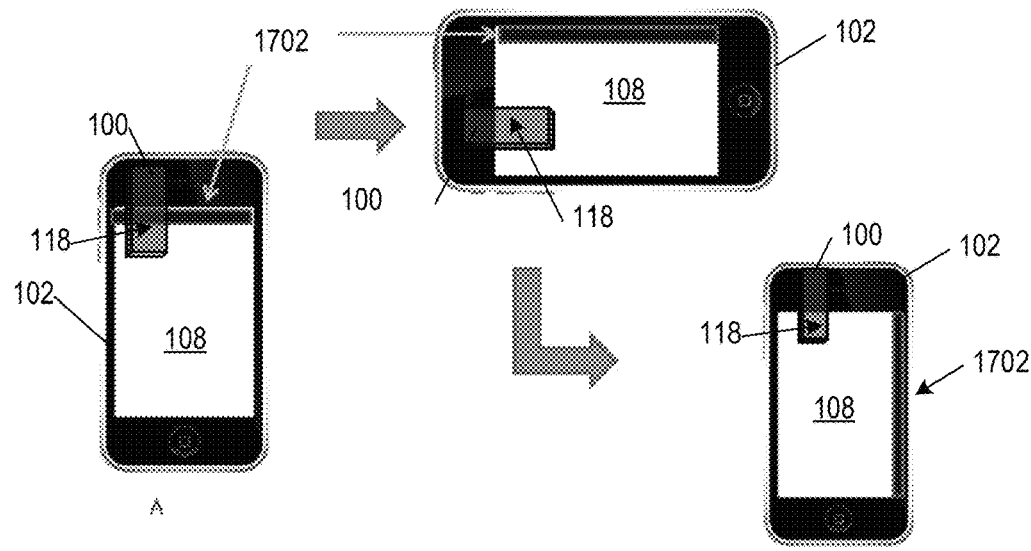
FIG. 17 illustrates limiting a notification to a specific edge of the mobile computing device of FIG. 1 in examples of the present disclosure.

FIG. 17 illustrates a banner 1702 that would normally appear at a short, top edge of mobile phone 102 in examples of the present disclosure. As can be seen, banner 1702 would supersede light source area 118 also located on the short, top edge of screen 108. To avoid this, processor 112 locks mobile phone 102 in a landscape orientation even though photometric test strip analyzer 117 is actually running in a portrait orientation so banner 1702 appears at a long, side edge of screen 108. In other examples, processor 112 may change banner 1702 to an alert that appears in the middle of screen 108 instead of the short, top edge of screen 108. In other examples, when an operating system (OS) of mobile phone 102 permits, processor 112 may temporarily turn off or postpone notifications for other applications.

Referring back to FIG. 16, block 1604 may be followed by block 1606.

In block 1606, processor 112 performs a measurement pre-test to determine if mobile phone 102 is has the proper setup to determine the analyte property. Block 1606 may be followed by block 1608.

In block 1608, processor 112 determines if mobile phone 102 has passed the measurement pre-test. If not, block 1608 may be followed by block 1610. Otherwise block 1608 may be followed by block 1612.

In block 1610, processor 112 suggests changing the setup of mobile phone 102 by displaying a message on screen 108.

Figure 18:
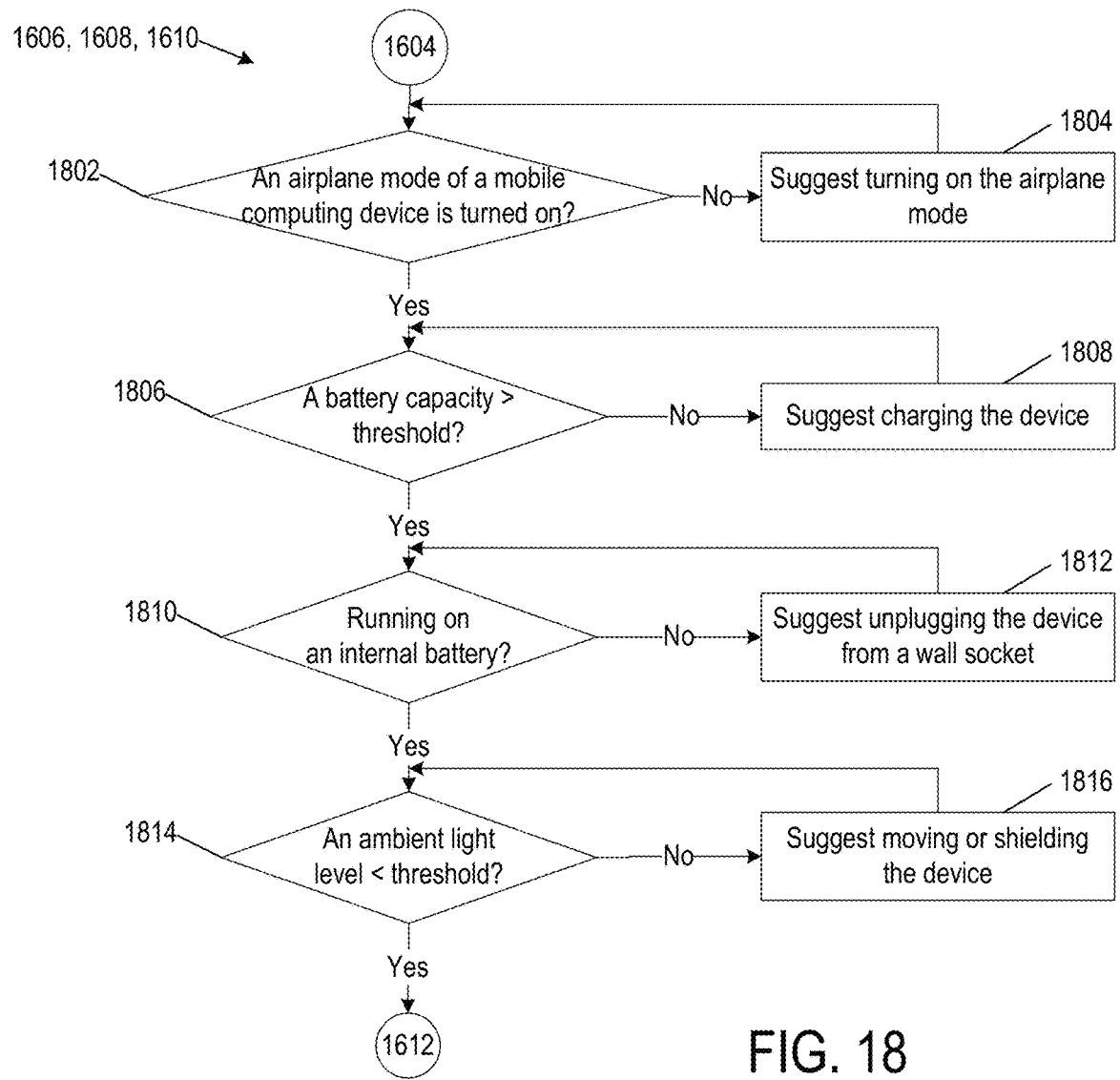
FIG. 18 is flowchart of a method for implementing a measurement pre-test in the method of FIG. 16 in examples of the present disclosure.

FIG. 18 is flowchart of a method 1800 for implementing blocks 1606, 1608, and 1610 of method 1600 in examples of the present disclosure. Method 1800 may begin in block 1802 following block 1604 in method 1600.

In block 1802, processor 112 determines if an airplane mode is turned on for mobile phone 102. In the airplane mode, wireless connections and services are turned off so mobile phone 102 does not receive calls that would otherwise interrupt photometric test strip analyzer 117 (FIG. 1) and change the color of the light provided by light source area 118 (FIG. 1). If mobile phone 102 is not in the airplane mode, block 1802 may be followed by block 1804. Otherwise block 1802 may be followed by block 1806.

In block 1804, processor 112 suggests turning on the airplane mode by displaying a message on screen 108. Processor 112 may exit photometric test strip analyzer 117 or loop back to block 1802 to determine if the user has turned on the airplane mode. Alternatively processor 112 may automatically turn on the airplane mode and proceed to block 1806.

In block 1806, processor 112 determines if a battery capacity of mobile phone 102 is greater than a threshold. The threshold ensures mobile phone 102 has sufficient energy to determine the analyte property. If the battery capacity of mobile phone 102 is not greater than the threshold, block 1806 may be followed by block 1808. Otherwise block 1806 may be followed by block 1810.

In block 1808, processor 112 suggests charging mobile phone 102 by displaying a message on screen 108. Processor 112 may exit photometric test strip analyzer 117 or loop back to block 1806 to determine if the battery capacity is now greater than the threshold.

In block 1810, processor 112 determines if mobile phone 102 is running on an internal battery. When mobile computing device 102 is plugged into a wall socket, power fluctuation in the mains may vary the light provided by light source area 118 (FIG. 1) of screen 108 (FIG. 1) and sensor response of camera 104 (FIG. 1). If mobile phone 102 is not running on the internal battery, block 1810 may be followed by block 1812. Otherwise block 1810 may be followed by block 1814.

In block 1812, processor 112 suggests unplugging mobile phone 102 from the wall socket by displaying a message on screen 108. Processor 112 may exit photometric test strip analyzer 117 or loop back to block 1810 to determine if mobile phone 102 is now running on the internal battery.

In block 1814, processor 112 determines if an ambient light level is less than a threshold. When the ambient light level is high, it may leak into test strip module 100 and interfere with the light provided by light source area 118 of screen 108. Processor 112 may sense the ambient light level using camera 104, which is not covered by any test strip module at this point, and optionally record it for further use in the measurement phase. If the ambient light level is not less than the threshold, block 1814 may be followed by block 1816. Otherwise block 1814 may be followed by block 1612 in method 1600.

In block 1816, processor 112 suggests moving or shielding mobile phone 102 by displaying a message on screen 108. Processor 112 may exit photometric test strip analyzer 117 or loop back to block 1814 to determine if the ambient light level is now less than the threshold.

Referring back to FIG. 16, in block 1612, processor 112 detects test strip 204 in test strip module 100 after test strip module 100 is placed on mobile phone 102. Processor 112 detects test strip 204 by using camera 104 to capture an image of the interior of test strip module 100 and light source area 118 illuminating the interior of test strip module 100, and finding a candidate in the image that resembles test strip 204 based on shape, color, or color intensity.

Figure 19:
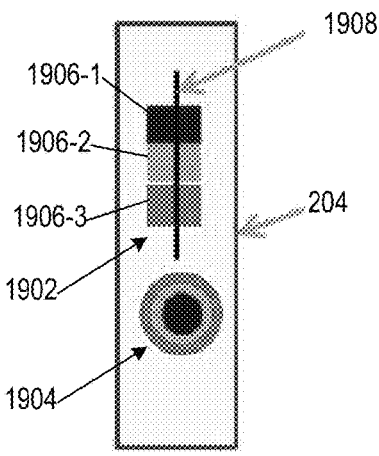
FIG. 19 shows a test strip in examples of the present disclosure.

FIG. 19 shows test strip 204 in examples of the present disclosure. Test strip 204 includes a reaction area 1902 and a color calibration area 904. Reaction area 1902 may include subareas 1906-1, 1906-2, and 1906-3 (collectively as "subareas 1906") targeting different value ranges of an analyte property or properties of different analytes. Subareas 1906 may have the same color or different colors before a sample is introduced. Color calibration area 1904 may have a known color or color intensity, or include subareas of known colors or color intensities.

Once processor 112 (FIG. 1) find a candidate in the image that resembles test strip 204, processor 112 takes a cross-section 1908 of an area where reaction area 1902 should be located on the candidate and determines if cross-section 1908 includes sections with different colors matching the different colors of subareas 1906-1, 1906-2, and 1906-3.

Referring back to FIG. 16, in block 1614, processor 112 determines if test strip 204 is correctly positioned. Test strip 204 is aligned with camera 104 and light source area 118 when cross-section 1908 includes the different color sections matching the different colors of subareas 1906. If not, block 1614 may be followed by block 1616. Otherwise block 1614 may be followed by block 1618.

In block 1616, processor 112 suggests moving test strip module 100 by displaying a message on screen 108. Processor 112 may loop back to block 1612 to determine if test strip 204 is now correctly positioned.

In block 1618, processor 112 locks a white balance setting of camera 104 to a known value. When an OS of mobile phone 102 does not allow processor 112 to set the white balance setting, processor 112 may temporarily lock the white balance setting to the known value by causing camera 104 to capture a first image under low light (e.g., with light source area 118 turned off) and then immediately capturing a second image under normal lighting (e.g., with light source area 118 turned on). In a short period of time immediately after camera 104 captures the first image under low light, the white balance setting will remain at the known value so the second image is also captured at this know white balance setting. For example, the white balance setting under low light may provide a 1:1:1 red, green, and blue (RGB) ratio. Block 1618 may be followed by block 1620.

In block 1620, processor 112 performs a calibration of a lighting condition inside test strip module 100. Block 1620 may be followed by block 1622.

In block 1622, processor 112 determines if the lighting condition inside test strip module 100 passed the calibration. If not, block 1622 may be followed by block 1624. Otherwise block 1622 may be followed by block 1626.

In block 1624, processor 112 suggests moving mobile phone 102 or shielding test strip module 100 by displaying a message on screen 108. Processor 112 may loop back to block 1620 to determine if the lighting condition inside test strip module 100 now passes the calibration.

In block 1626, processor 112 performs a measurement of test strip 204. In the measurement, processor 112 uses camera 104 to capture an image of a reaction area on test strip 204, determines one or more color characteristics of the reaction area, corrects the one or more color characteristics, correlates the corrected one or more color characteristics to the analyte property. Block 1626 may be followed by block 1628.

In block 1628, processor 112 displays the result on screen 108.

Figure 20:
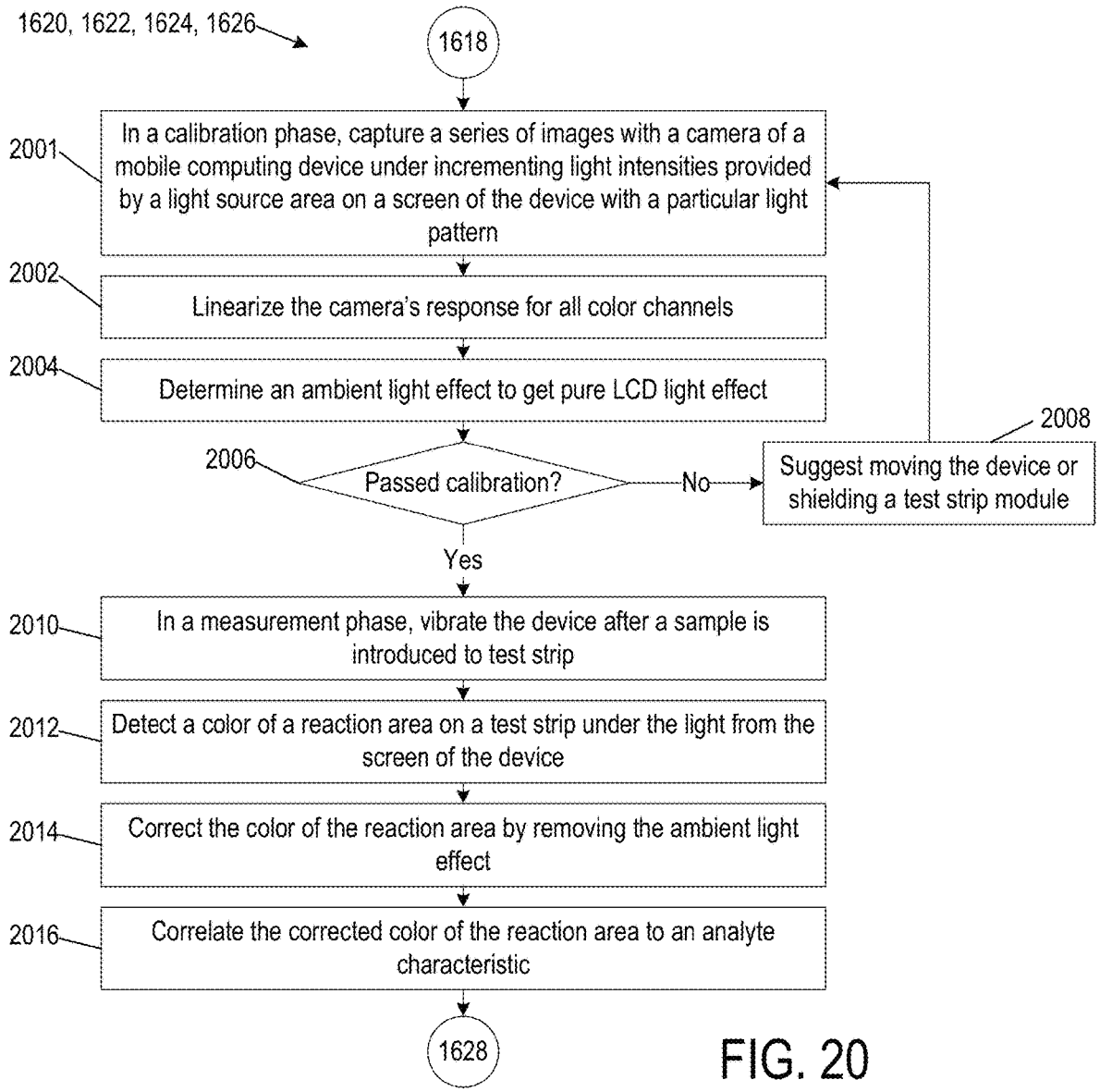
FIG. 20 is flowchart of a method for implementing a calibration and a measurement in the method in FIG. 16 in examples of the present disclosure.

FIG. 20 is flowchart of a method 2000 for implementing blocks 1620, 1622, 1624, and 1626 of method 1600 in examples of the present disclosure. Method 2000 may begin in block 2001 following block 1618 in method 1600.

In block 2001, processor 112 enters a calibration phase and uses camera 104 to capture a series of images under light of a certain pattern and incrementing intensities provided by light source area 118. Light source area 118 increments from off to fully on. In some examples, the light intensities include 0, 0.2, 0.4, 0.6, 0.8, and 0.9. In other examples the incrementing light intensities include only 0 and 0.9. The light pattern may square, triangular, or another shape that evenly illuminates test strip 204 (e.g., FIG. 19) due to the interior geometry of test strip module 100. Block 2001 may be followed by block 2002.

In block 2002, processor 112 linearizes the camera's response for all color channels based on the images captured in block 2001. Image sensors of camera 104 may have non-linearity at the extremes of their range. Linearizing the camera's response corrects the non-linearity to provide actual color channel values. Block 2002 may be followed by block 2004.

In block 2004, processor 112 determines an ambient light effect based on color calibration area 1904 (e.g., FIG. 19) of test strip 204 captured on a first image taken with light source area 118 off (e.g., light intensity=0) and a second image taken with light source area 118 on (e.g., light intensity=0.9) in the series of images. Color calibration area 1904 has an actual color channel value that is known to processor 112.

Figure 21:
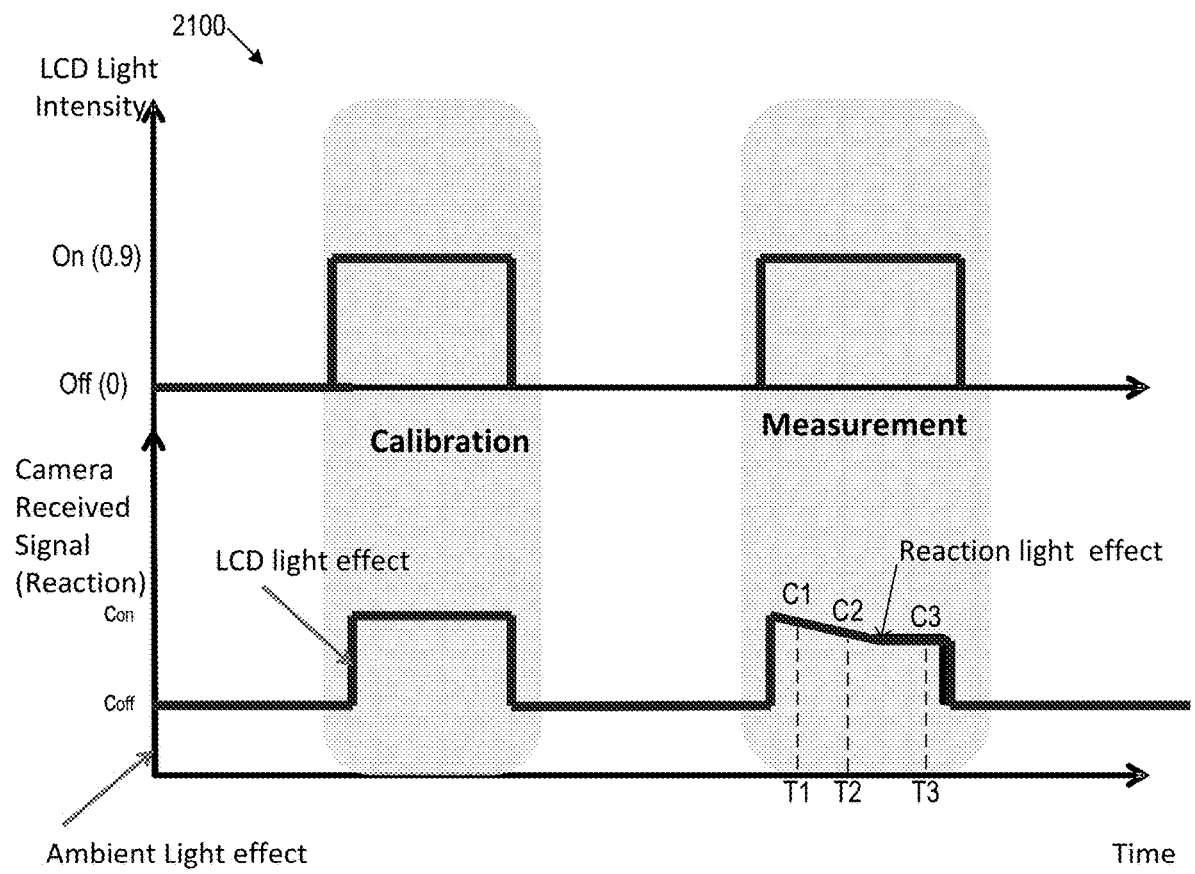
FIG. 21 illustrates a combined chart plotting light intensity and camera response in a calibration phase and a measurement phase in examples of the present disclosure.

FIG. 21 illustrates a combined chart 2100 with an upper chart plotting light intensity over time and a lower chart plotting a camera response for a color channel over the same time in a calibration phase and a measurement phase in examples of the present disclosure. The values in chart 2100 are provided for illustrative purposes. The camera response may be an average of the color channel values of areas in the first and the second images that correspond to color calibration area 1904 with a known color channel value.

In the example calibration phase, the camera response has a color channel value of $C_{off}$ when light source area 118 is off (e.g., light intensity=0) due to ambient light leaking into test strip module 100. The camera response has a value of $C_{on}$ when light source area 118 is on (e.g., light intensity is 0.9). The following formula may be used to determine a corrected color channel value without the ambient light effect:

$$C_{corrected} = (C_{detected} - C_{on})\frac{C_{actual}}{C_{on} - C_{off}}, \text{ or}$$

$$C_{corrected} = (C_{detected} - C_{off})\frac{C_{actual}}{C_{on} - C_{off}},$$

where $C_{off}$ is the detected color channel value of color calibration area 1904 with light source area 118 off during the calibration phase, $C_{on}$ is the detected color channel value of color calibration area 1904 with light source area 118 on during the calibration phase, $C_{actual}$ is the actual color channel value of color calibration area 1904, $C_{detected}$ is the detected color channel value of a desired area (e.g., reaction area 1902 in FIG. 19) with light source area 118 on during the measurement phase, and $C_{corrected}$ is the corrected color channel value of the desired area during measurement phase.

Referring back to FIG. 20, block 2004 may be followed by block 2006.

In block 2006, processor 112 determines if the ambient light effect is greater than a threshold. The ambient light effect is represented by detected color channel value $C_{detected}$ with light source area 118 off during the calibration phase. A high ambient light effect may result in detected color channel values that cannot be corrected. When the ambient light effect is greater than the threshold, block 2006 may be followed by block 2008. Otherwise block 2006 may be followed by block 2010.

In block 2008, processor 112 suggests moving mobile phone 102 or shielding test strip module 100 by displaying a message on screen 108.

Figure 22:
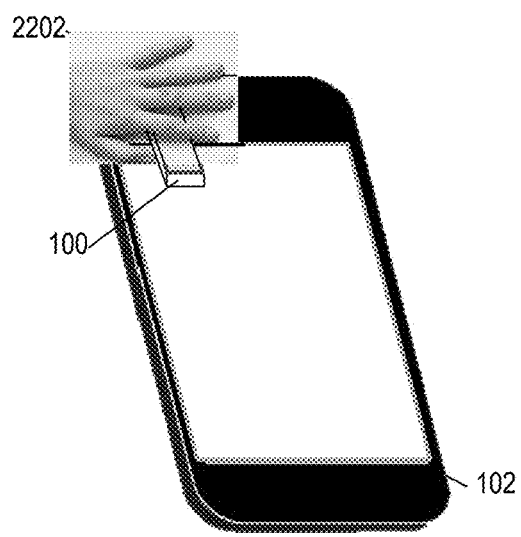
FIGS. 22 and 23 show how a test strip module may be shielded in examples of the present disclosure.
Figure 23:
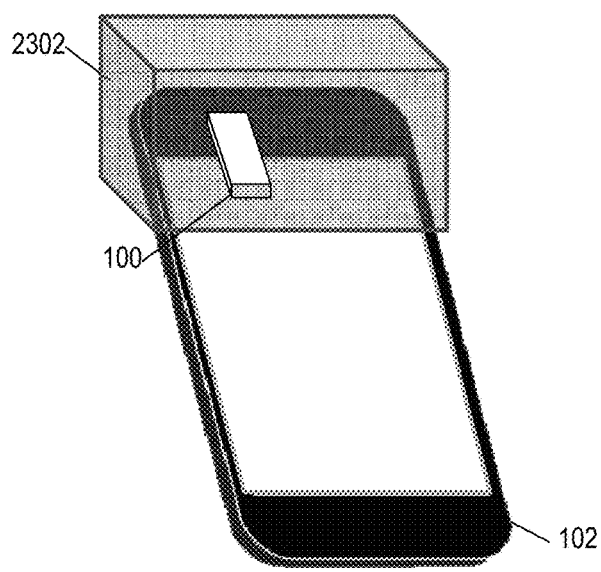

FIGS. 22 and 23 show how test strip module 100 may be shielded in examples of the present disclosure. In FIG. 22, a user places her hand 2202 over test strip module 100 to shield it from the ambient light. In FIG. 23, the user places a box top 2302 over test strip module 100. Box top 2030 may be part of the packaging for test strip module 100.

Referring back to FIG. 20, processor 112 may loop back to block 2001 recalibrate camera 104.

In block 2010, processor 112 enters the measurement phase and causes mobile phone 102 to vibrate after the sample is introduced to a sample inlet on test strip module 100. The vibration helps to move the sample through sample channel 1104 (FIG. 11) to test strip 204. Block 2010 may be followed by block 2012.

In block 2012, processor 112 captures at least one image of reaction area 1902 on test strip 204 with light source area 118 on and detects at least one color characteristic of the reaction area. In some examples of the present disclosure, processor 112 captures two images of reaction area 1902 at times T1, T2 and detects two colors C1, C2 of reaction area 1902 as shown in FIG. 21. Block 2012 may be followed by block 2014. In some examples, processor 112 captures one image of the reaction area 1902 at T3 and detects a color C3 of reaction area 1902 as shown in FIG. 21.

In block 2014, processor 112 corrects the detected color or colors to remove the ambient light effect in their values. Block 2014 may be followed by block 2016.

In block 2016, processor 112 correlates the corrected color or colors to the analyte property. In the examples with two corrected colors, processor 112 determines a slope of the line between a first point (C1, T1) and a second point (C2, T2) and correlates the slope to the analyte property from a chart mapping slopes to analyte property values.

Figure 24:
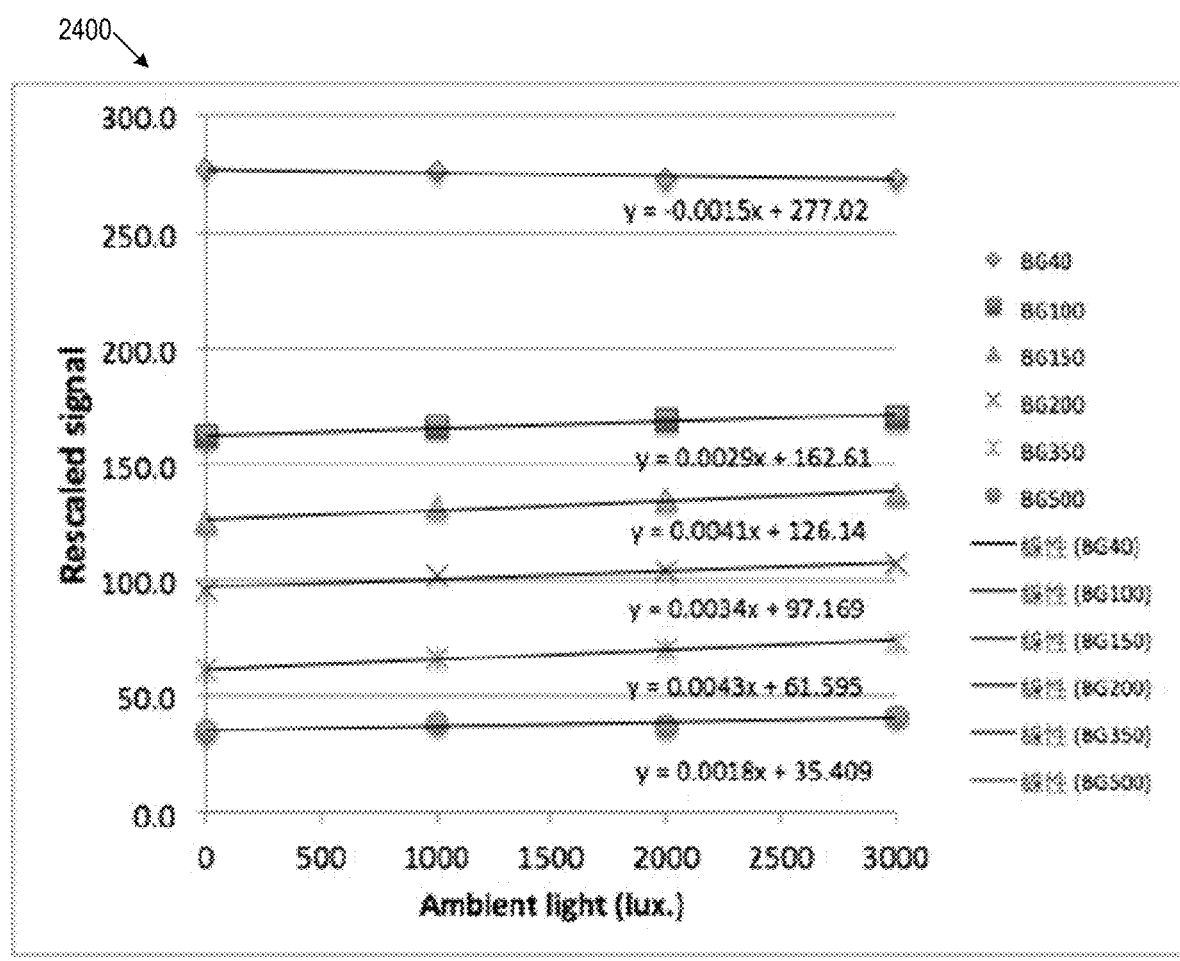
FIG. 24 is a chart that plots color values over ambient light levels for different values of an analyte property in examples of the present disclosure.

In some examples of the present disclosure, processor 112 does not correct the color of the reaction area by removing the ambient light effect. Instead processor 112 uses the known color or colors of color calibration area 1904 and the detected color or colors of calibration area 1904 to rescale a detected color of reaction area 1908. The rescaled color of reaction area 1908 would include the ambient light effect. Processor 112 then correlates the rescaled color and the ambient light level detected in block 1814 (FIG. 18) to the analyte property using a chart mapping rescaled color values and ambient light levels to analyte property values. FIG. 24 illustrates one such chart 2400 in examples of the present disclosure. In chart 2400, multiple lines representing different analyte properties (e.g., blood glucose levels) plot color values over the ambient light levels. Such charts may be experimentally determined for different mobile phones and stored with photometric test strip analyzer 117 or downloaded as needed.

Referring back to FIG. 20, block 2016 may be followed by block 1628 of method 1600.

Figure 25:
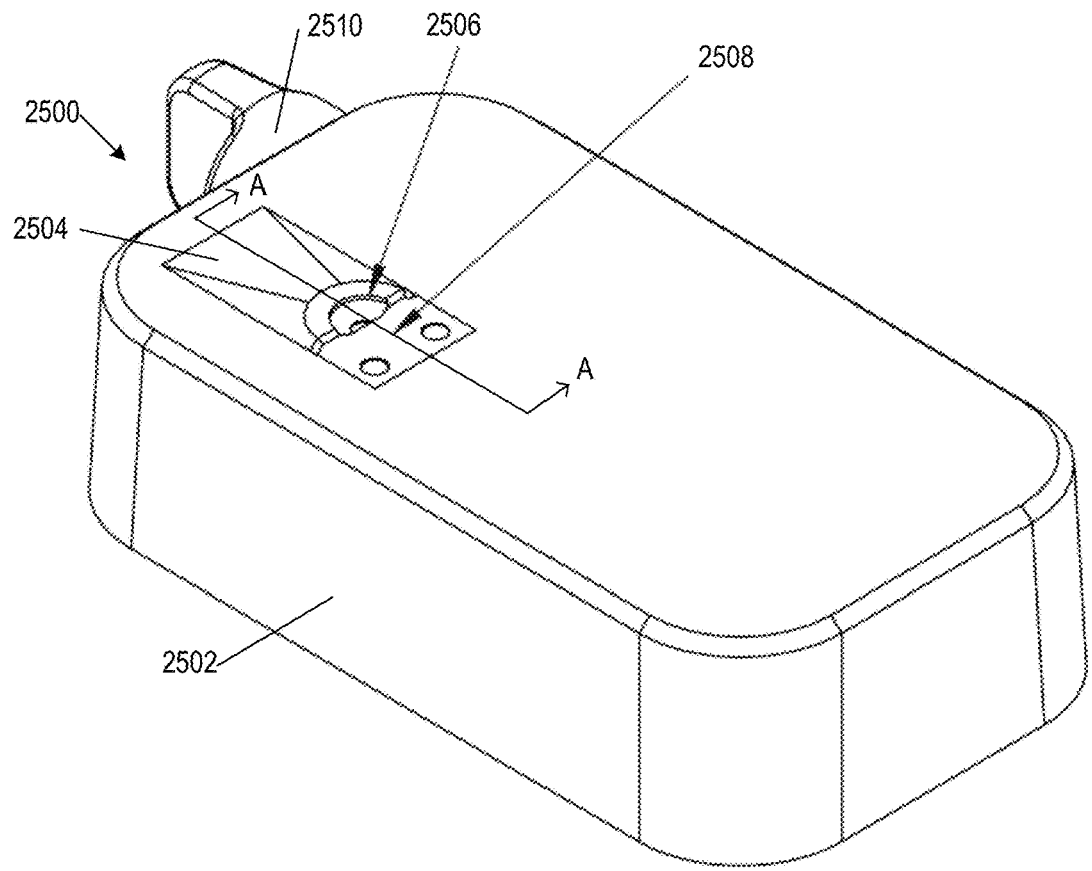
FIG. 25 is an isometric view of a variation of the test strip module of FIG. 1 in examples of the present disclosure.
Figure 26:
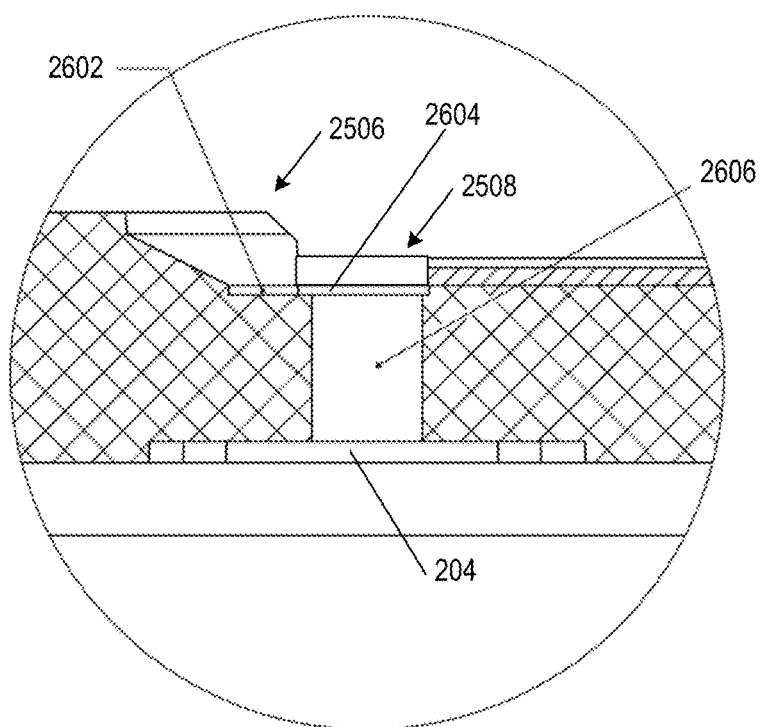
FIG. 26 is an enlarged cross-sectional view of the test strip module of FIG. 25 in examples of the present disclosure.

FIG. 25 shows a variation 2500 of test strip module 100 (FIG. 1) in examples of the present disclosure. FIG. 26 shows a partial cross-section of test strip module 100 in examples of the present disclosure. Test strip module 2500 has case 2502. The top of case 2502 defines a finger guide 2504 and a sample collector 2506. A fluid transport film 2508 is fixed to the top of case 2502 adjacent to sample collector 2506. A lancet cover 2510 may be fitted to case 2502 to hermetically protect a lancet inside case 2502.

Sample collector 2506 may have the shape of a halved funnel. Finger guide 2504 may be a V-shaped ramp with sidewalls that narrow toward the round edge of sample collector 2506, and the ramp slopes down toward the round edge of sample collector 2506. Fluid transport film 2508 abuts against the open half of the funnel shaped sample collector 2506. In use, user glides her finger along finger guide 2504 toward sample collector 2506 and then deposit a sample in sample collector 2506. Referring to FIG. 26, the sample would collect at the bottom 2602 of sample collector 2506. A hydrophilic layer 2604 on the back of fluid transport film 2508 is located adjacent to the bottom 2602 of sample collector 2506 and transports the sample laterally from bottom 2602 to a channel 2606 in case 2502. Channel 2606 is defined by case 2502 between hydrophilic layer 2604 and test strip 204. The sample travels from hydrophilic layer 2604 down channel 2606 to test strip 204. Fluid transport film 2508 may be Mylar with a hydrophilic coating 2604 on one side.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method for a mobile computing device to measure a test strip in a test strip module, the method comprising:
   in a calibration phase before a sample is introduced to a reaction area on the test strip, detecting with a camera on a face of the mobile computing device an ambient light effect from an ambient light leaking into the test strip module through an interface between a case of the test strip module and the face of the mobile computing device when the test strip module is mounted on the face of the mobile computing device, wherein detecting the ambient light effect comprises:
      capturing a series of images under incrementing light intensities;
      linearizing a response of the camera based on the series; and
      determining a formula for a corrected color based a first image in the series that is captured with the light source area off and a second in the series that is captured with the light source area on, comprising:

$$C_{corrected} = (C_{detected} - C_{on})\frac{C_{actual}}{C_{on} - C_{off}}, \text{ or}$$

$$C_{corrected} = (C_{detected} - C_{off})\frac{C_{actual}}{C_{on} - C_{off}},$$

where $C_{off}$ is a detected color of a color calibration area in the first image, $C_{on}$ is a detected color of the color calibration area in the second image, $C_{actual}$ is an actual color of the color calibration area, $C_{detected}$ is a detected color in a third image captured with the light source area on in the measurement phase, and $C_{corrected}$ is the corrected color value;

in a measurement phase after the sample is introduced to the reaction area on the test strip:
      illuminating the test strip with a light emitted by a light source area of a screen on the face of the mobile computing device, wherein the light source area corresponds to a portion of the screen;
      detecting with the camera one or more colors of the reaction area;
      correcting the detected one or more colors for the ambient light effect;
      correlating the corrected one or more colors to an analyte property; and
      displaying a value of the analyte property on the screen.

2. The method of claim 1, wherein correcting the detected one or more colors for the ambient light effect includes subtracting the ambient light effect from the detected color.

3. The method of claim 1, wherein correlating the corrected one or more colors to an analyte property comprises:
   determining a slope of a line between first and second points, the first point comprising a first detected color of a desired area and a first time at which the first detected color was captured in a first image during the measurement phase, the second point comprising a second detected color and a second time at which the second detected color was captured in a second image during the measurement phase; and
   correlating the slope to the value of the analyte property based on a chart.

4. The method of claim 1, wherein correlating the corrected one or more colors to an analyte property comprises:
   determining an ambient light level;
   determining a detected color of a desired area captured in an image during the measurement phase;
   using a known color or known colors of a color calibration area on the image to determine a rescaled color from the detected color; and
   correlating the ambient light level and the rescaled color to the value of the analyte property based on a chart.

5. The method of claim 1, further comprising performing a pre-test by:
   determining if an airplane mode of the mobile computing device is turned on, wherein the method proceeds to the calibration and the measurement phases when the airplane mode is turned on;
   determining if a battery capacity is greater than a first threshold, wherein the method proceeds to the calibration and the measurement phases when the battery capacity is greater than the first threshold;
   determining if the mobile computing device is running on an internal battery, wherein the method proceeds to the calibration and the measurement phases when the mobile computing device is running on the internal battery; or
   determining if an ambient light level is less than a second threshold, wherein the method proceeds to the calibration and the measurement phases when the ambient light level is less than the second threshold.

6. The method of claim 1, further comprising, prior to the calibration phase:
   determining if the test strip is correctly positioned, wherein the method proceeds to the calibration and the measurement phases when the test strip is correctly positioned.

7. The method of claim 6, wherein determining if the test strip is correctly positioned comprises identifying the test strip in an image based on a shape, a color, or a light intensity.

8. The method of claim 7, wherein determining if the test strip is correctly positioned comprises further comprises taking a cross-section of a reaction area on the test strip in the image and determining if sections of the cross-section have colors that correspond to actual colors of the reaction area.

9. The method of claim 1, further comprising, in the calibration phase:
   determining if the ambient light effect is greater than a threshold; and
   when the ambient light effect is greater than the threshold, displaying on the screen a suggestion to move the mobile computing device or shield the test strip module.

10. The method of claim 9, wherein the suggestion comprises shielding the test strip module with a hand or a box top that is part of a packaging of the test strip module.

11. The method of claim 1, further comprising, before operating in the calibration phase and the measurement phase, limiting any notification to a location away from the light source area of the screen.

12. The method of claim 11, wherein limiting any notification comprises locking an orientation of the mobile computing device so notifications appear along one edge of the screen instead of another edge that includes the light source area of the screen.

13. The method of claim 1, further comprising, locking a white balance for the camera by taking an image with low light immediately before taking a second image with a light emitted by the light source area of the screen.

14. The method of claim 1, further comprising, in the measurement phase, causing the mobile computing device to vibrate.

* * * * *